(12) United States Patent
Maffei et al.

(10) Patent No.: US 11,241,452 B2
(45) Date of Patent: Feb. 8, 2022

(54) ORAL COMPOSITIONS FOR THE TREATMENT OF GASTROESOPHAGEAL REFLUX

(71) Applicant: ALFASIGMA S.P.A., Bologna (IT)

(72) Inventors: Paola Maffei, Bologna (IT); Marco Mascagni, Bologna (IT); Giuseppe Claudio Viscomi, Bologna (IT)

(73) Assignee: ALFASIGMA S.P.A., Bologna (IT)

( * ) Notice: Subject to any disclaimer, the term of this patent is extended or adjusted under 35 U.S.C. 154(b) by 53 days.

(21) Appl. No.: 16/349,711

(22) PCT Filed: Sep. 18, 2018

(86) PCT No.: PCT/EP2018/075200
§ 371 (c)(1),
(2) Date: May 14, 2019

(87) PCT Pub. No.: WO2019/063363
PCT Pub. Date: Apr. 4, 2019

(65) Prior Publication Data
US 2019/0314402 A1    Oct. 17, 2019

(30) Foreign Application Priority Data

Sep. 28, 2017   (IT) .................. 102017000108526

(51) Int. Cl.

| | | |
|---|---|---|
| A61K 47/26 | (2006.01) | |
| A61K 47/20 | (2006.01) | |
| A61K 31/726 | (2006.01) | |
| A61K 47/12 | (2006.01) | |
| A61P 1/04 | (2006.01) | |
| A61K 9/00 | (2006.01) | |
| A61K 47/10 | (2017.01) | |
| A61K 47/36 | (2006.01) | |

(52) U.S. Cl.
CPC ............ *A61K 31/726* (2013.01); *A61K 9/006* (2013.01); *A61K 9/0095* (2013.01); *A61K 47/10* (2013.01); *A61K 47/12* (2013.01); *A61K 47/36* (2013.01); *A61P 1/04* (2018.01)

(58) Field of Classification Search
CPC ...... A61K 31/726; A61K 47/36; A61K 47/10; A61K 9/006; A61K 9/0095; A61K 47/12; A61P 1/04
USPC .......................................................... 514/54
See application file for complete search history.

(56) References Cited

U.S. PATENT DOCUMENTS

| | | | |
|---|---|---|---|
| 7,504,387 B2 | 3/2009 | Marcum | |
| 2006/0292184 A1 | 12/2006 | Richardson et al. | |
| 2009/0081133 A1* | 3/2009 | Bottoni ................... | A61P 31/10 424/49 |
| 2012/0238630 A1 | 9/2012 | Viscomi et al. | |
| 2013/0183325 A1 | 7/2013 | Bottoni et al. | |
| 2013/0272970 A1* | 10/2013 | Pimenta ................. | A61K 8/044 424/52 |
| 2014/0107064 A1 | 4/2014 | Pizzoni | |

FOREIGN PATENT DOCUMENTS

| | | |
|---|---|---|
| EP | 1173218 B1 | 1/2002 |
| EP | 1898876 B1 | 3/2008 |
| EP | 1614431 B1 | 12/2008 |
| EP | 2296670 B1 | 3/2011 |
| EP | 2435021 B1 | 4/2012 |

OTHER PUBLICATIONS

Glossary of medical education terms, Institute of International Medical Education. http://www.iime.org/glossary.htm Accessed in Mar. 2013. (Year: 2013).*
Savarino et al. A review of pharmacotherapy for treating gastroesophageal reflux disease (GERD). Expert Opinion on Pharmacotherapy, 2017, vol. 18, No. 13, 1333-1343 (published online: Aug. 7, 2017) (Year: 2017).*
Response to Written Opinion of PCT/EP2018/075200 dated Jan. 11, 2019.
Search Report and Written Opinion of PCT/EP2018/075200 dated Nov. 22, 2018.
Chin-Hsun Yi et al.,"Atypical symptoms in patients with gastroesophageal reflux disease" J Neurogastroenterol Motil, 2012; 18: 278-283.
Cho, Y.S., et al., "Prevalence and clinical spectrum of gastroesophageal reflux: a population-based study in Asan-si", KoreaAm J Gastroenterol 2005;100:747-753.
Fini A et al., "Mucoadhesive gels designed for the controlled release of chlorhexidine in the oral cavitY".Pharmaceutics 2011, 3, 665-679.
Frye J.W et al., "Extraesophageal GERD" Gastroenterol Clin North Am 2008; 37: 845-858.
Hassan E.E., et al., "A simple rheological method for the in vitro assessment of mucin-polymer bioadhesive bond strength" .Pharm. Res. 1990; 7 (5): 491-495.
Jaspersen D. et al., "Prevalence of extra-oesophageal manifestations in gastro-oesophageal reflux disease: an analysis based on the ProGERD Study" Aliment Pharmacol Ther 2003;17: 1515-1520.
Katz P. O. et al., "Review article: acid-related disease—what are the unmet clinical needs?" Alim Pharm Ther 2006, 23 (Suppl 2), 9-22.
Kulig M. et al., "Quality of life in relation to symptoms in patients with gastro-oesophageal reflux disease—an analysis based on the ProGERD initiative". Aliment Pharmacol Ther 2003; 18: 767-776.
OECD Guidelines for the testing of Chemicals No. 428. Apr. 13, 2004.
Vakil N. et al., "The Montreal definition and classification of gastroesophageal reflux disease: a global evidence-based consensus". Am J Gastroenterol 2006; 101: 1900-1920.

* cited by examiner

*Primary Examiner* — Yih-Horng Shiao
(74) *Attorney, Agent, or Firm* — Silvia Salvadori, P.C.; Silvia Salvadori (57) ABSTRACT

The present invention describes a mucoadhesive composition comprising chondroitin sulfate, xyloglucan and glycerol for use in the treatment and prevention of gastroesophageal reflux. It is also described a process for preparing such composition, a dosage form for its administration and a kit comprising the same.

13 Claims, 5 Drawing Sheets

ORAL COMPOSITIONS FOR THE TREATMENT OF GASTROESOPHAGEAL REFLUX

This application is a U.S. national stage of PCT/EP2018/075200 filed on 18 Sep. 2018, which claims priority to and the benefit of Italian Patent Application No. 102017-000108526 filed on 28 Sep. 2017, the contents of which are incorporated herein by reference in their entireties.

FIELD OF THE INVENTION

The invention describes a mucoadhesive composition comprising chondroitin sulphate, xyloglucan and glycerol for use in the treatment and prevention of gastroesophageal reflux.

The invention also describes a process for the preparation of such composition, a dosage form for its administration and a kit comprising such composition.

BACKGROUND

Gastroesophageal reflux disease (GERD) is a very common disorder which occurs with its predominant symptom, i. e. stomach heartburn, due to the passage of gastric content into the esophagus, where it irritates the mucosa causing pain and discomfort for a few minutes or hours.

Stomach burning can be caused by many factors such as eating habits, different kinds of foods, pregnancy and side effects of medicines. Moreover, the stress amplifies the sensitivity to the acid, and fat accumulation in overweight or obese subjects increase the abdominal pressure, favouring the passage of gastric content into the esophagus.

Although the most commonly recognized symptoms of GERD are heartburn and/or acid regurgitation, retrosternal pain and acid taste in the mouth GERD is often associated with other clinical manifestations such as globus sensation, non-obstructive dysphagia, chest pain chronic cough, hiccup, dyspepsia or belching [Frye J W et al, Gastroenterol Clin North Am 2008; 37: 845-858].

Although evidence-based consensus includes cough, irritating cough, hoarseness, laryngitis, asthma and dental erosion as atypical manifestations, other atypical symptoms are also common with significant impact in GERD patients [Cho Y S, et al. Am J Gastroenterol 2005; 100:747-753]. Since most patients with GERD have no erosions on endoscopy, GERD has been further classified into erosive reflux disease (ERD) and non-erosive reflux disease (NERD) [Vakil N, et al. Am J Gastroenterol 2006; 101:1900-1920]. It is evident that NERD is not a milder form of GERD, since similar impact on quality of life has been demonstrated irrespective of the presence of mucosal injury [Kulig M, et al. Aliment Pharmacol Ther 2003; 18: 767-776].

It has been reported that that atypical symptoms are slightly greater in patients with ERD than NERD in a European multicenter study [Jaspersen D, et al. Aliment Pharmacol Ther 2003; 17: 1515-1520]. A population-based study in Korean has confirmed that typical reflux symptoms, i.e. heartburn and regurgitation, retrosternal pain and acid taste in the mouth are significantly associated with atypical symptoms. Of interest is that increased frequency of typical GERD symptoms was found more in patients with atypical symptoms than those without any atypical symptoms [Chin-Hsun Yi et al. J Neurogastroenterol Motil, 2012; 18: 278-283].

Proton pump inhibitors (PPIs) represent the first-choice medical treatment for gastroesophageal reflux disease, in that they are able to provide an 80-85% healing rate for oesophageal lesions, including ulcers. Nevertheless, the PPIs do not resolve the incidence of complications and patients often continue to report symptoms and problems that decrease their quality of life.

Also, patients with non-erosive reflux exhibit a reduced relief after treatment with PPIs, and Katz P. O. et al. in Alim Pharm Ther 2006, 23 (Suppl 2), 9-22 report that only 20% of these patients have therapeutic recovery, but most of them relapse within 6 months. Recent studies have shown that, in patients with NERD, not only acid reflux but also non-acid reflux can induce histopathological alterations. For example, the dilatation of intercellular space between the cells adjacent to the oesophageal epithelium represents a feature that has become an index to diagnose microscopic oesophagitis.

Enlarged intercellular spaces cause an increase of permeability favouring the hydrogen ions and other substances penetration, i. e. pepsin and bile, into the esophageal submucosa, reaching nerve fibres. The stimulation of these fibers generates the characteristic symptom of heartburn. Several studies suggest that acid reflux and duodenal-gastric reflux may exert a synergistic action in the formation of lesions. Furthermore, pepsin exerts a role in the pathogenesis of GERD extra-esophageal manifestations.

In the market there are several medicines and medical devices for the treatment of gastroesophageal reflux containing chondroitin sulphate and alginates.

Chondroitin sulphate (CS) is a natural glycosaminoglycan present in the extracellular matrix. It is a linear heteropolysaccharide consisting of repeating disaccharide units of glucuronic acid and galactosamine, which is commonly sulphated at C-4 and/or C-6 of galactosamine. Natural chondroitin sulphate, extracted from animal mucosa, normally has a molecular weight from 10,000 to 50,000 Dalton. CS provides elasticity to cartilage, controls the resistance thereof and protects the epithelium from acid attacks and the urothelium from potassium.

In pathologies, wherein the concentration of chondroitin sulphate is low, such as gastritis or interstitial cystitis, the administration of chondroitin sulphate-based products helps to reduce the symptoms caused by reflux and decreases inflammation.

Alginate is extracted from the algae cell walls, looks like a gum, and the suspension formed by sodium alginate, when ingested, reacts with the hydrochloric acid present in the stomach, forming a protective film at the cardias level. The gelatinized structure of sodium alginate is characterized by neutral pH values, floating above the food in the stomach, preventing gastroesophageal reflux. Alginate is comprised together with sodium bicarbonate in the marketed Gaviscon® product.

EP 2296670 B1, corresponding to US 2014/0107064, describes a combination of hyaluronic acid and chondroitin sulfate together with a bioadhesive agent for the prevention or treatment of esophagitis. The bioadhesive agent is selected from poloxamer, polymers of polyvinylpyrrolidone and cellulose derivatives.

EP 2435021 B1 describes the use of compositions containing hyaluronic acid, chondroitin sulfate and aluminium hydroxide for the treatment of gastric disease such as gastritis and duodenal endothelium damages.

U.S. Pat. No. 7,504,387 describes the use of a solution containing hyaluronic acid and chondroitin sulfate for the treatment of interstitial cystitis.

EP 1173218 B1 and EP 1614431 B1 describe the use of compositions comprising an alginate and two kinds of gums; a first gum chosen between xanthan gum and carrageenan gum and a second gum chosen between galactomannan and glucomannan. These compositions are characterized by high bioadhesive properties and are able to adhere to the oesophagus walls, but they present high viscosity values. Due to their high viscosity the composition are difficult to be prepared and poorly accepted by patients.

EP 1898876, B1 corresponding to US 2013/0183325, describes mucoadhesive compositions containing glycerol and xyloglucan suitable for the application to human mucous membranes, for use as moisturizing and softening agents or as pharmaceutical release system for local and/or systemic use.

US 2006/292184 discloses mucoadhesive compositions for use in the treatment and prevention of gastroesophageal reflux comprising glycerol.

The term xyloglucan refers to a class of polysaccharides structurally related to cellulose and intimately associated with it in the cell wall of higher plants. They are also one of the main components, probably with energy reserve function, of plant seeds such as *Tamarindus indica*, indigenous to India and Southeast Asia, *Detarium senegalense* and *Afzelia africana*, widespread both in central and eastern Africa, and *Hymenaea courbaril*, widespread in central and south America. Xyloglucans are characterized by a main chain of (1,4)-β-D-glucan substituted with side chains of α-D-xylopyranose and β-D-galactopyranosyl-(1,2)-α-D-xylopyranose, linked by α(1,6) bond to glucan residues. The distribution of residues in the side chains is different in xyloglucans of different species.

The compositions of EP 1898876 B1 include purified xyloglucan in an aqueous solution at concentrations from 0.05 to 5% by weight and glycerol at a concentration from 10% to 70% by weight. This document does not refer to gastrointestinal mucosae nor to the treatment of pathologies associated with oesophageal reflux.

Therefore, there is a need of effective composition for the treatment of gastroesophageal reflux, able to provide a barrier and/or a binder to the aggressive components of the gastric reflux, containing acids and pepsin, and to ensure an effective treatment of lesions and ulcers of the oesophageal mucosa, as well as to provide symptomatic relief to oesophagitis induced by radiotherapy or radio-chemotherapy.

Furthermore, it would be useful to have compositions containing natural and effective agents for the treatment of oesophageal reflux to be administered alone or in combination with other drugs with good compliance by patients.

Additionally, it would be useful to have compositions maintaining the effect with reduced risk of adverse events.

SUMMARY OF THE INVENTION

The object of the invention is to provide a mucoadhesive pharmaceutical composition for use in the treatment and prevention of gastroesophageal reflux, comprising chondroitin sulphate, xyloglucan and glycerol.

The composition for the use of the invention comprises chondroitin sulphate at a concentration ranging from 0.5 to 5% (w/v), xyloglucan at a concentration ranging from 0.05 to 5% (w/v) and glycerol at a concentration ranging from 10 to 70% (w/v), referred to the volume of the final composition, and optionally pharmaceutically acceptable excipients.

The composition for the use according to the present invention may be in unit dosage form or in syrup for oral administration.

According to an aspect of the invention, the composition has viscosity values ranging from 1 to 15 Pa·s when subjected to shear rates from 0 to 1.5 s$^{-1}$, and viscosity values lower than 1.5 Pa·s when subjected to shear rates higher than 1.5 s$^{-1}$.

According to another aspect, the composition of the present invention has a pH value from 4.5 to 6.5.

According to another aspect of the invention, the pharmaceutical composition is useful in the treatment and in the prevention of erosive gastroesophageal reflux and of non-erosive gastroesophageal reflux, caused by bad food habits, side effects of drugs, pregnancy and obesity.

The pharmaceutical composition comprising chondroitin sulphate, xyloglucan and glycerol according to the invention is further useful in providing relief to oesophagitis induced by radiotherapy or radio-chemotherapy.

The composition of the invention may be comprised in a medicine or in a medical device for use in the treatment and prevention of erosive (GERD) and non-erosive (NERD) gastroesophageal reflux, causing diseases such as esophagitis, endothelial damage, erosions, ulcers and gastritis, including drug-induced adverse damages.

The pharmaceutical composition according to the invention is useful in the treatment of all the typical symptoms common in erosive reflux disease (ERD) and non-erosive reflux disease (NERD), such as heartburn, acid regurgitation, retrosternal pain and acid taste in the mouth, and in the treatment of the main atypical symptoms of erosive and non-erosive form of GERD, i.e., cough, irritating cough, hoarseness, laryngitis, asthma and dental erosion, preferably of irritating cough, hoarseness.

A further object of the invention is to provide a process for preparing a composition comprising chondroitin sulphate, xyloglucan and glycerol, comprising the steps of:

heating an amount of glycerol to obtain a final concentration from 10 to 70% (w/v) to a temperature from 60 to 90° C. and adding an amount of xyloglucan such as to obtain a final concentration from 0.05 to 5% (w/v);

lowering the temperature to below 30° C.;

adding to the homogeneous solution an amount of chondroitin sulphate such as to obtain a final concentration from 0.5 to 5% (w/v).

DETAILED DESCRIPTION OF THE INVENTION

It is an object of the invention to provide a mucoadhesive and gastroprotective composition comprising chondroitin sulphate, xyloglucan and glycerol in defined amounts, useful for the treatment and prevention of gastroesophageal reflux.

Chondroitin sulphate included in the composition of the present invention is preferably used as alkaline salt, preferably sodium salt, extracted from animal mucosa.

As used in the sense of the description with the term "treatment" should be intended "cure" or "remission" of a pathological condition, or disease, as well as prevention or mitigation, reduction, improvement of the symptoms correlated with the recognized pathological conditions at the end of the treatment period with respect to the baseline.

Xyloglucan included in the composition of the invention is preferably extracted by tamarind seeds, purified and protein free, prepared as described in patent EP 1898876 B1.

The composition of the invention comprises chondroitin sulphate at a concentration from 0.5 to 5% (w/v), xyloglucan at a concentration from 0.05% to 5% (w/v) and glycerol at a concentration from 10 to 70% (w/v) referred to the volume of final composition, together with pharmaceutically acceptable excipients.

In a preferred aspect, the composition comprises chondroitin sulphate at a concentration from 1 to 5% (w/v), xyloglucan at a concentration from 0.1 to 1% (w/v) and glycerol at a concentration from 10 to 50% (w/v), referred to the volume of final composition.

Excipients for liquid formulations, normally aqueous formulations, suspensions or solutions may comprise buffering agents, such as for example phosphates and bicarbonates; antioxidants, such as for example sodium metabisulphite, sodium sulphite, citric acid; thickening agents, such as for example cellulose derivatives, xanthan gum, Arabic gum, starches; preservatives, such as methylparaben, ethylparaben, sodium ethylenediaminetetraacetate, sodium benzoate, potassium sorbate; flavouring and sweetening agents.

Sweetening agents can be natural, with or without sugars, such as, for example, sucrose, dextrose, xylitol, mannitol and sorbitol, or synthetic products, such as, for example, saccharin and aspartame.

Flavouring agents are agents that increase taste, such as fruits, plants and flower extracts. The composition of the invention is characterized by high acceptability and palatability, even without the addition of flavourings and sweetening agents.

The composition may contain preservative agents in a concentration from 0.001 to 0.1% (w/v), sweetening agents from 0 to 5.0% (w/v), flavourings from 0 to 1.5% (w/v), thickening agents from 0.1 to 3.0% (w/v) and buffering agents from 0.01 to 2.0% (w/v) referred to the volume of final composition.

The composition of the invention is characterized by pH values from 4.5 to 6.5, preferably by pH values from 5.0 to 6.0.

For example, a composition for the use according to the invention comprises sodium chondroitin sulphate from 0.1 to 0.5 g, xyloglucan from 0.01 to 0.1 g and glycerol from 1 to 5 g. Furthermore, such composition may comprise pharmaceutically acceptable excipients, including preservatives, buffering agents and thickeners, and be diluted with water. The composition can be diluted up to a final volume of 10 ml or 100 ml or a desired volume.

In one aspect, the composition according to the invention contains 0.3 g sodium chondroitin sulphate, 0.04 g xyloglucan, 2 g glycerol, 0.01 g sodium bicarbonate, 0.0083 g xanthan gum, 0.2 g xylitol, 0.02 g sodium benzoate, 0.015 g orange flavour, 0.01 g citric acid, 0.02 g potassium sorbate, 0.086 g hydroxypropyl methylcellulose and demineralized water up to 10 ml (Composition 1, Example 1).

Said composition is preferably dosed twice daily (BID) or three times daily (TID). Said composition is preferably for use in the treatment of non-erosive gastroesophageal reflux disease and it can be administered BID, TID or to the need.

This composition can be intended as a unitary composition or its amount can be proportionally increased for multiple doses compositions.

It has been found that the composition of the present invention comprising chondroitin sulphate from 0.5 to 5% (w/v), xyloglucan from 0.05 to 5% (w/v) and glycerol from 10 to 70% (w/v), referred to the volume of the final composition, provides solutions characterized by a viscoelastic behaviour. Such solutions are characterized by Storage Modulus values (G') which decrease at the increase of the applied stress and by Loss Modulus values (G") which increase at the decrease of the applied stress. The storage modulus G' represents the elastic portion of the viscoelastic behaviour, which describes the solid-state behaviour of the sample. The loss modulus G" characterizes the viscous portion of the viscoelastic behaviour, which can be seen as the liquid-state behaviour of the sample.

The compositions are characterized by non-Newtonian rheological behaviour, wherein the viscosity changes depend on the applied force, wherein at increased share rate values applied, lower values of viscosity are shown. This feature is useful for a formulation for oral administration, having liquid properties to be easily ingested, and solid properties to stay adhered to oesophageal mucosa.

To evaluate the effect of the association of chondroitin sulphate with xyloglucan and glycerol in the composition of the invention, the activity of the present composition was compared with that of a composition wherein xyloglucan and glycerol are replaced with an agent having mucoadhesive properties, such as a poloxamer (comparison Composition 2).

The association of chondroitin sulphate with xyloglucan and glycerol provides compositions characterized by a viscoelastic behaviour with viscosity values in the range from about 1 to about 15 Pa·s when subjected to shear rates from 0 to 1.5 $s^{-1}$, and viscosity values lower than about 1.5 Pa·s when subjected to shear rates higher than 1.5 $s^{-1}$.

The viscosity of Composition 2 is instead independent on the applied shear rate.

When a shear strain from 1 to 100% is applied to the composition of the invention, its G' values vary in the range from 4 to 1 Pa and the G" values vary in the range from 6 to 4 Pa.

The composition of the invention comprising chondroitin sulphate from 0.5 to 5% (w/v), xyloglucan from 0.05 to 5% (w/v) and glycerol from 10 to 70% (w/v) provides a synergistic mucoadhesive effect when compared to action of the single components.

The mucoadhesivity was determined by rheological measurements and by ex-vivo experiments.

The viscosity of the composition of the invention when mixed with mucin in a 1:1 weight ratio is higher than the sum of the single viscosities of the composition and of mucin, demonstrating a close interaction among the components of the composition with mucin.

Rheological synergism and normalized rheological synergism ($\Delta\eta/\eta$) between the mucoadhesive composition and mucin are established.

The normalized rheological synergism was calculated by experimental measures, as the difference between the viscosity of the mixture composition/mucin and the sum of the single viscosities of the mucoadhesive composition and of mucin, with respect to the viscosity of the mucoadhesive composition (a reference for the calculation can be found in Fini A et al, Pharmaceutics 2011, 3, 665-679).

The rheological synergism between mucin and a polymeric composition is a recognized in vitro measure of the mucoadhesion of the composition itself, as described in Hassan E E, Gallo J M, Pharm. Res. 1990; 7 (5): 491-495.

The rheological synergism values for the composition according to the invention (Composition 1) and mucin in a 1:1 weight ratio increase when the applied shear rate are increased, while the viscosity value decreases. The lack of linearity between viscosity and mucoadhesion is consistent with the non-Newtonian behaviour of the composition of the present invention.

In the comparative composition, wherein glycerol and xyloglucan were replaced with a poloxamer, the rheological synergism values decreased at the increase of the applied shear rate.

The composition of the invention resulted to adhere and protect the esophageal mucosa from acidic and/or irritating agents by forming a film layer. From the microscopic analysis of esophageal mucosa tissues colored with Evans Blue, it can be observed that in the mucosa fragments not previously treated with the composition of the invention, the dye penetrates into the layers of the stratified squamous epithelium, spreading in the entire lamina, i.e. it goes beyond the muscularis mucosae down to the submucosa; instead, in the fragments pre-treated with the composition of the invention, the dye signal shows that it does not enter all the layers of the stratified epithelium.

The composition of the invention remains adherent to the gastroesophageal mucosa and is able to protect it down to the submucous membrane; it resists the wash-away effect of liquid foods, beverages and saliva, thus allowing the ulcers healing and recovery.

The composition according to the invention has been analysed in a three-dimensional model, providing a useful tool for assessing the safety of the finished product and its biocompatibility as a medical device, also allowing to define the nature of its mechanism of action by providing the proof of its superficial action on body barriers.

By using such 3D model, the permeability of the compositions of the present invention to the passage of a reference low lipophilic compound was assessed. Caffeine is a reference compound according to the Guideline for the Testing of Chemicals (OECD No. 428, Apr. 13, 2004, skin absorption, in vitro method). The compositions of the present invention were analysed in comparison to a saline solution (negative control) and vaseline (positive control). The composition of the invention, comprising chondroitin sulphate at a concentration from 0.5 to 5% (w/v), glycerol at a concentration from 10 to 70% (w/v) and xyloglucan at a concentration from 0.05 to 5% (w/v), provides a barrier to irritating agents, and a lower permeability in comparison to composition wherein chondroitin sulphate at the same concentrations is associated with a mucoadhesive agent such as Poloxamer 407® (Composition 2).

The composition of the invention is effective in the treatment of oesophageal reflux by forming a film barrier on the oesophageal mucosa, and it does not cause any cell damage, otherwise critical to essential physiological processes. This has been demonstrated with trans-epithelial electrical resistance (TEER) measurements and cell permeability assessment by fluorescence measurements. The composition of the invention maintains the stability of the barrier created on the oesophageal mucosa, important for all physiological processes. The TEER measured after a 6 hours treatment with the composition of the invention shows similar values to those given by the tissue treated with saline solution, demonstrating that the paracellular flow at the epithelial mucosa level has not been influenced. This is also confirmed by fluorescence measurements using Lucifer Yellow dye, a fluorescent molecule which the cell membrane is impermeable to. From the fluorescence measurements of two compartments separated by the epithelial tissue treated with the composition of the invention, the integrity of cell junctions was confirmed.

The following figures explain the subject-matter of the present invention.

The composition of the invention may be comprised in a drug product or in a medical device for use in the treatment and prevention of pathologies related to erosive (GERD) and non-erosive gastroesophageal reflux disease (NERD), esophagitis, duodenal endothelium damages, like erosions and ulcers, gastritis, including drug adverse side effects. Such composition is useful for the treatment of gastroesophageal reflux, by reducing symptoms such as gastric pyrosis, epigastric pain, burns, retrosternal pain, acid regurgitation, acid taste in the mouth, irritable or stinging cough and hoarseness.

The composition of the invention can be used to protect oesophageal mucosa from erosion by foods, drugs and acid refluxes, that can penetrate and cause irritation, or by disorders caused by pregnancy, obesity and stress.

Protective action on the mucous membrane occurs without altering its physiological mechanism, with no side effects and with good compliance by the subjects.

The composition of the present invention is prepared by a process wherein xyloglucan is added to pre-heated glycerol at a temperature from 60 to 90° C., and to the homogeneous solution so obtained, at a temperature lower than 30° C., chondroitin sulphate is added. To the homogeneous composition buffering agents, antioxidants, thickening agents, preservatives, flavouring and sweetening agents are optionally added.

The composition of the present invention is prepared by a process comprising a step of heating at a temperature from 60 to 90° C. an amount of glycerol such as to obtain a final concentration from 10 to 70% (w/v) and the addition under stirring of an amount of xyloglucan such as to obtain a final concentration from 0.05 to 0.5% (w/v) of the total composition. The mixture is then kept under stirring until complete dissolution. Thickening agents can be optionally added, and then the mixture is diluted with water pre-heated at a temperature from 60 to 90° C., in amounts up to 5 times the amount of glycerol, according to the desired final volume. The homogeneous solution is then cooled to room temperature, lower than 30° C.

Furthermore, the preparation process comprises the step of adding to the homogeneous solution at a temperature lower than 30° C. an amount of chondroitin sulphate such as to obtain a final concentration from 0.5 to 5% (w/v) of total composition.

Pharmaceutically or alimentary acceptable excipients or carrier can be added.

The prepared solution is preferably partitioned into single dose packs, vials, or bottles for syrup, for example for paediatric dosages.

The composition of the invention, subjected to stability test both at 25° C. and 40° C., has shown to be stable at both temperatures for at least 3 months.

The composition of the present invention has good palatability and tolerability by individuals and has no toxic effects.

The composition of the invention may be administered at any time of the day, for example after main meals and before bedtime, once, twice, three times daily or to the need. The composition has no side effects, it is well tolerated and it may be administered for one week or longer and the administration may be in repeated cycles.

The composition of the invention in a clinical study carried out in patients with atypical symptoms associated to NERD, such as, hoarseness and irritating cough resulted effective when administered both two and 3 time daily, with a significant reduction of the symptoms and an increased quality of life.

The composition of the invention allows for a rapid and effective administration both for prolonged treatment and for extemporaneous use.

The composition of the invention may be administered in combination with pharmaceutical agents for treating gastroesophageal reflux, such as proton pump inhibitors (PPIs), or prokinetic or anti-acid drugs or others.

The compositions of the present invention may be included in kits as single dose packs, sticks-pack or vials for single or multiple dose, for oral administration.

EXAMPLES

Example 1: Preparation of a Composition According to the Invention (Composition 1)

In a heating mixer an amount of 30 kg of glycerol was heated at the temperature of about 80° C., then 1.29 kg of hydroxypropyl methylcellulose, 0.6 kg of xyloglucan and 0.125 kg of xanthan gum were added to the glycerol under stirring. The mixture was kept under stirring for about 20 minutes until complete homogenization. Then, 40 litres of water at about 80° C. were added and the stirring was prolonged for further about 20 minutes until complete dissolution of the components. About 120 litres of water at about 80° C. were added to the solution so obtained, and the temperature was lowered below 30° C. A mixture of 4.5 kg sodium chondroitin sulphate; 3.0 kg xylitol; 0.15 kg sodium bicarbonate; 0.3 kg sodium benzoate; 0.3 kg potassium sorbate; 0.18 kg orange flavour and 0.15 kg citric acid were then added under stirring.

The solution was brought to 150 litres volume with water and was divided in 10 ml stick packs.

The solution is characterized by a pH value of 5.5±0.2 and a viscosity of 1.6 Pa·s when subjected to a shear rate of 1 s$^{-1}$.

The unitary composition (concentration g/ml) of the stick-packs of Composition 1 are shown in Table 1.

TABLE 1

| Component (Composition 1) | Concentration (g/10 ml stick-pack) | Concentration % (w/v) |
|---|---|---|
| Sodium chondroitin sulphate | 0.3 | 3 |
| Xyloglucan | 0.04 | 0.4 |
| Glycerol | 2.0 | 20 |
| Sodium bicarbonate | 0.01 | 0.1 |
| Xanthan gum | 0.0083 | 0.083 |
| Xylitol | 0.2 | 2 |
| Sodium benzoate | 0.02 | 0.2 |
| Orange flavour | 0.015 | 0.15 |
| Citric acid | 0.01 | 0.1 |
| Potassium sorbate | 0.02 | 0.2 |
| Hydroxypropyl methylcellulose | 0.086 | 0.86 |
| Demineralized water | q.s. up to 10 ml | |

Example 2: Preparation of a Gastroprotective Composition (Composition 2—Comparison)

In a mixer, 312 g sodium chondroitin sulphate, 124 g sodium hyaluronate, 2248 g xylitol, and 5 litres of water were added under stirring and the solution was kept at 60° C. under stirring until dissolution. Then, 270 g Poloxamer 407®, 250 g polyvinylpyrrolidone, 10 g sodium bicarbonate, 9 g sodium benzoate, 2 g red grape flavour, 18 g potassium sorbate, 4M hydrochloric acid q. s. to pH 5.0±0.2 and demineralized water up to 10 litres were added.

The suspension was kept under stirring for 15 minutes at room temperature and then divided into 10 ml stick packs.

The unitary composition of Composition 2 is shown in Table 2.

TABLE 2

| Component (Composition 2) | Concentration (g/10 ml) | Concentration % (w/v) |
|---|---|---|
| Sodium chondroitin sulphate | 0.312 | 3.12 |
| Sodium hyaluronate | 0.124 | 1.24 |
| Poloxamer 407 ® | 0.270 | 2.7 |
| Sodium bicarbonate | 0.01 | 0.1 |
| Polyvinylpyrrolidone | 0.250 | 2.5 |
| Xylitol | 2.248 | 22.48 |
| Sodium benzoate | 0.009 | 0.09 |
| Red grape flavour | 0.002 | 0.02 |
| Potassium sorbate | 0.018 | 0.18 |
| Hydrochloric acid 4M | q.s. up to pH 5.0 ± 0.2 | |
| Demineralized water | q.s. up to 10 ml | |

The composition has a viscosity of 0.0463 Pa·s when subjected to a shear rate of 1 s$^{-1}$.

Example 3: Determination of Rheological Parameters of Compositions 1 and 2

A) Determination of Viscosity

Viscosity values of Composition 1, prepared according to Example 1, and Composition 2, prepared according to Example 2, were measured at 37° C. by an Anton Paar Rheometer, MCR 101 model, with a flat-cone geometry of 50 mm diameter.

Figure 1:
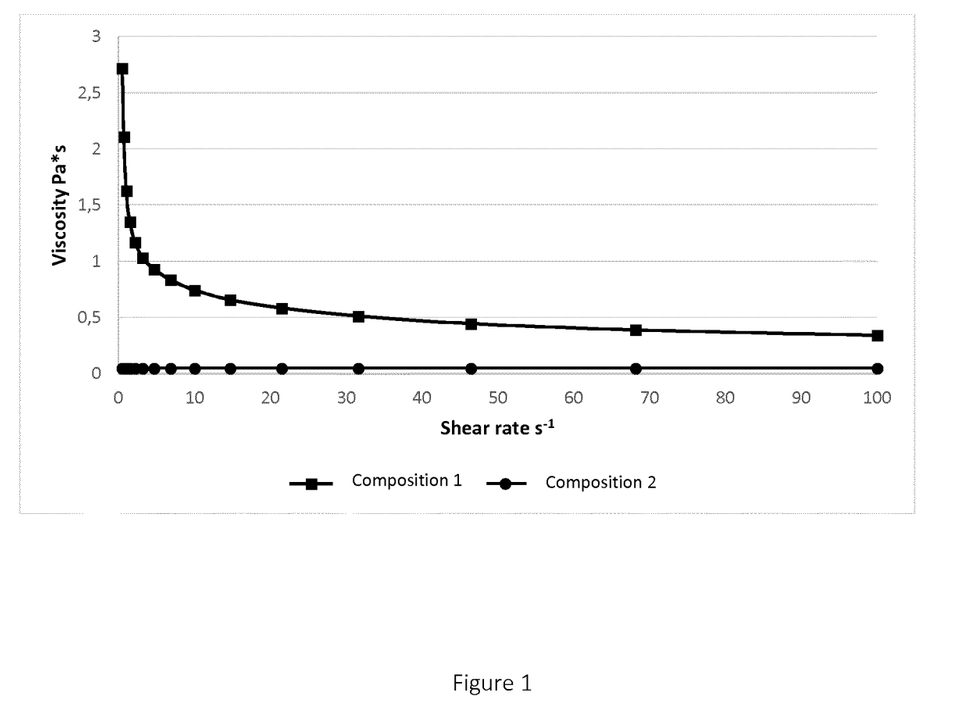
FIG. 1 shows the viscosity of composition 1 (invention) and composition 2 (comparative).

Table 3 reports the viscosity values as a function of increasing shear rates for Compositions 1 and 2 and they are reported in FIG. 1.

TABLE 3

| Shear rate (s$^{-1}$) | Viscosity Composition 1 (Pa · s) | Viscosity Composition 2 (Pa · s) |
|---|---|---|
| 0.00996 | 6.82 | <LOQ |
| 0.0146 | 9.2 | <LOQ |
| 0.0215 | 10.2 | <LOQ |
| 0.0315 | 10.3 | <LOQ |
| 0.0463 | 9.79 | <LOQ |
| 0.0679 | 8.84 | <LOQ |
| 0.0999 | 7.62 | <LOQ |
| 0.147 | 6.03 | <LOQ |
| 0.215 | 4.79 | <LOQ |
| 0.316 | 3.49 | <LOQ |
| 0.464 | 2.72 | 0.0470 |
| 0.682 | 2.11 | 0.0455 |
| 1.0 | 1.63 | 0.0463 |
| 1.47 | 1.35 | 0.0469 |
| 2.15 | 1.17 | 0.0474 |
| 3.16 | 1.03 | 0.0475 |
| 4.64 | 0.931 | 0.0477 |
| 6.81 | 0.835 | 0.0482 |
| 10 | 0.743 | 0.0484 |
| 14.7 | 0.658 | 0.0486 |
| 21.5 | 0.583 | 0.0487 |
| 31.6 | 0.511 | 0.0486 |
| 46.4 | 0.445 | 0.0484 |
| 68.1 | 0.389 | 0.0483 |
| 100 | 0.340 | 0.0483 |

LOQ = Limit of Quantification

B) Determination of Storage (G') and Loss (G") Modulus

The G' and G" values were obtained by an Anton Paar Rheometer, MCR 101 model, at 37° C. with a flat-cone geometry of 50 mm diameter.

Table 4 reports the G' and G" values of Compositions 1 and 2.

TABLE 4

| Strain % applied | Storage Modulus G' (Composition 1) (Pa) | Storage Modulus G' Composition 2 (Pa) | Loss Modulus G" Composition 1 (Pa) | Loss Modulus G" Composition 2 (Pa) |
|---|---|---|---|---|
| 1 | 2.91 | <LOQ | 5.07 | 0.372 |
| 1.46 | 2.95 | <LOQ | 5.07 | 0.322 |
| 2.14 | 2.96 | <LOQ | 5.05 | 0.318 |
| 3.17 | 2.96 | <LOQ | 5.05 | 0.326 |
| 4.64 | 2.97 | <LOQ | 5.05 | 0.314 |
| 6.82 | 2.94 | <LOQ | 5.06 | 0.309 |
| 10 | 2.91 | <LOQ | 5.06 | 0.305 |
| 14.7 | 2.85 | <LOQ | 5.05 | 0.303 |
| 21.5 | 2.77 | <LOQ | 5.03 | 0.304 |
| 31.7 | 2.67 | <LOQ | 4.99 | 0.303 |
| 46.5 | 2.53 | <LOQ | 4.94 | 0.304 |
| 68.1 | 2.34 | <LOQ | 4.85 | 0.303 |
| 100 | 2.08 | <LOQ | 4.69 | 0.303 |

Figure 2:
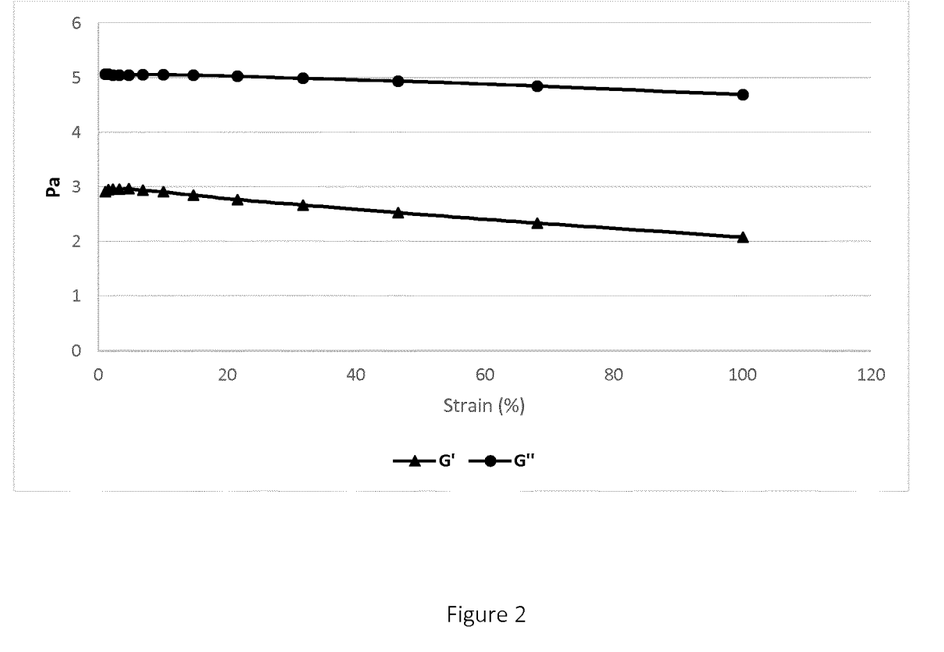
FIG. 2 shows the storage modulus (G') and the loss modulus (G") of composition 1 (invention).

FIG. 2 shows Storage Modulus (G') and Loss Modulus (G") of Composition 1 as a function of the percentage of the applied strain shear.

Figure 3:
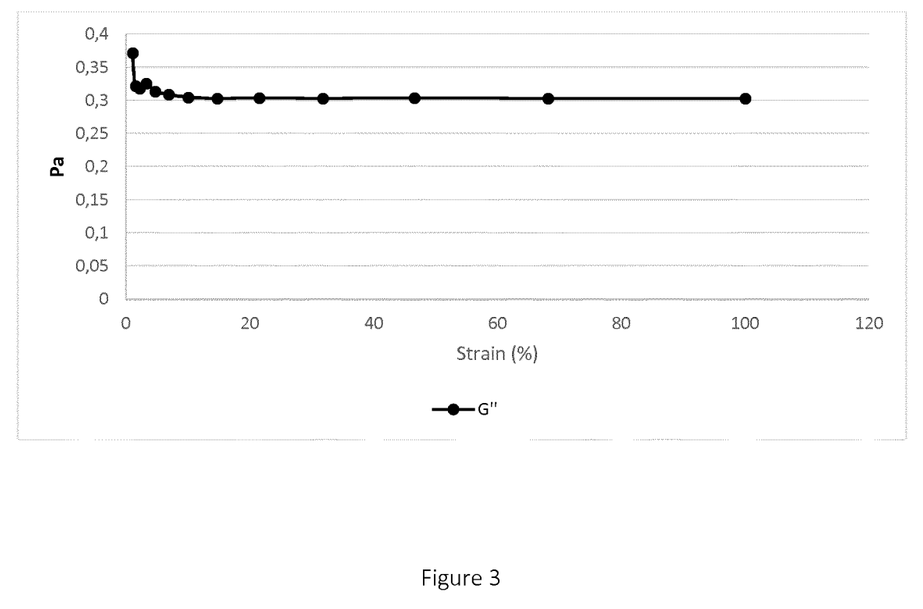
FIG. 3 shows the loss modulus (G") of composition 2 (comparative).

FIG. 3 shows Loss Modulus (G") of Composition 2 as a function of the percentage of the applied strain shear.

Example 4: Determination of Mucoadhesivity by Rheological Measurements

A) Determination of Viscosity

The following aqueous solutions (Sol.) A-F were prepared. During the preparation procedure the ingredients were maintained under stirring for about 30 minutes.

To perform the determination mucin from porcine stomach type II, (Sigma-Aldrich) was used.

| Solutions | Composition |
|---|---|
| Sol. A | Mucin at 6% (w/w) |
| Sol. B | Mucin at 12% (w/w) |
| Sol. C | Composition 1 [1:1 diluted with water (w/w)] |
| Sol. D | Composition 1 [1:1 diluted with mucin 12% (w/w)] |
| Sol. E | Composition 2 [1:1 diluted with water (w/w)] |
| Sol. F | Composition 2 [1:1 diluted with mucin 12% (w/w)] |

Table 5 reports the viscosity values of solutions A, C and D as a function of the different shear rates applied. The fourth column of the Table reports the value of Viscosity (C+A), i.e. the sum of the viscosity of Solution C and the viscosity of Solution A. The sixth column of the Table reports the normalized rheological synergism values ($\Delta\eta/\eta$), obtained by applying the formula:

$$\Delta\eta/\eta(\text{Composition 1-}mucin) = \frac{\text{Viscosity } Sol.D - (\text{Viscosity } Sol.C + \text{Viscosity } Sol.A)}{\text{Viscosity } Sol.C}$$

TABLE 5

Rheological Synergism Composition 1-mucin (Solution D)

| Shear rate ($s^{-1}$) | Viscosity Solution C (Pa·s) | Viscosity Solution A (Pa·s) | Viscosity (C + A) (Pa·s) | Viscosity Solution D (Pa·s) | $\Delta\eta/\eta$ (Composition 1-mucin) |
|---|---|---|---|---|---|
| 3.16 | 0.1210 | 0.0345 | 0.1555 | 0.343 | 1.55 |
| 4.64 | 0.0989 | 0.0340 | 0.1329 | 0.312 | 1.81 |
| 6.81 | 0.0850 | 0.0331 | 0.1181 | 0.284 | 1.95 |
| 10 | 0.0744 | 0.0323 | 0.1067 | 0.259 | 2.04 |
| 14.70 | 0.0656 | 0.0312 | 0.0968 | 0.237 | 2.14 |
| 21.50 | 0.0589 | 0.0301 | 0.0890 | 0.217 | 2.17 |
| 31.60 | 0.0533 | 0.0293 | 0.0826 | 0.199 | 2.18 |
| 46.40 | 0.0483 | 0.0279 | 0.0762 | 0.182 | 2.19 |
| 68.10 | 0.0437 | 0.0270 | 0.0707 | 0.165 | 2.16 |
| 100 | 0.0398 | 0.0261 | 0.0659 | 0.149 | 2.08 |

Table 6 reports the viscosity values of solutions A, E and F as a function of the different shear rates applied. The fourth column of the Table reports the value of Viscosity (E+A), i.e. of the sum of the viscosity of Solution E and the viscosity of Solution A. The sixth column of the Table reports the normalized rheological synergism values ($\Delta\eta/\eta$), obtained by applying the formula:

$$\Delta\eta/\eta(\text{Composition 2-}mucin) = \frac{\text{Viscosity } Sol.F - (\text{Viscosity } Sol.E + \text{Viscosity } Sol.A)}{\text{Viscosity } Sol.E}$$

TABLE 6

Rheological Synergism Composition 2-mucin (Solution F)

| Shear rate ($s^{-1}$) | Viscosity Solution E (Pa·s) | Viscosity Solution A (Pa·s) | Viscosity (E + A) (Pa·s) | Viscosity Solution F (Pa·s) | $\Delta\eta/\eta$ (Composition 2-mucin) |
|---|---|---|---|---|---|
| 3.16 | 0.00762 | 0.0345 | 0.0421 | 0.1210 | 10.35 |
| 4.64 | 0.00762 | 0.0340 | 0.0416 | 0.1190 | 10.15 |
| 6.81 | 0.00756 | 0.0331 | 0.0407 | 0.1170 | 10.09 |
| 10 | 0.00766 | 0.0323 | 0.0400 | 0.1150 | 9.79 |
| 14.70 | 0.00788 | 0.0312 | 0.0391 | 0.1120 | 9.25 |
| 21.50 | 0.00809 | 0.0301 | 0.0382 | 0.1090 | 8.75 |
| 31.60 | 0.00819 | 0.0293 | 0.0375 | 0.1060 | 8.36 |
| 46.40 | 0.00813 | 0.0279 | 0.0360 | 0.1020 | 8.11 |
| 68.10 | 0.00806 | 0.0270 | 0.0351 | 0.0979 | 7.79 |
| 100 | 0.00807 | 0.0261 | 0.0342 | 0.0937 | 7.37 |

Table 5 shows increased rheological synergism values when increased shear rate were applied for Composition 1. Differently, Table 6 shows the lack rheological synergism for Composition 2 when increased shear rate were applied.

Figure 4:
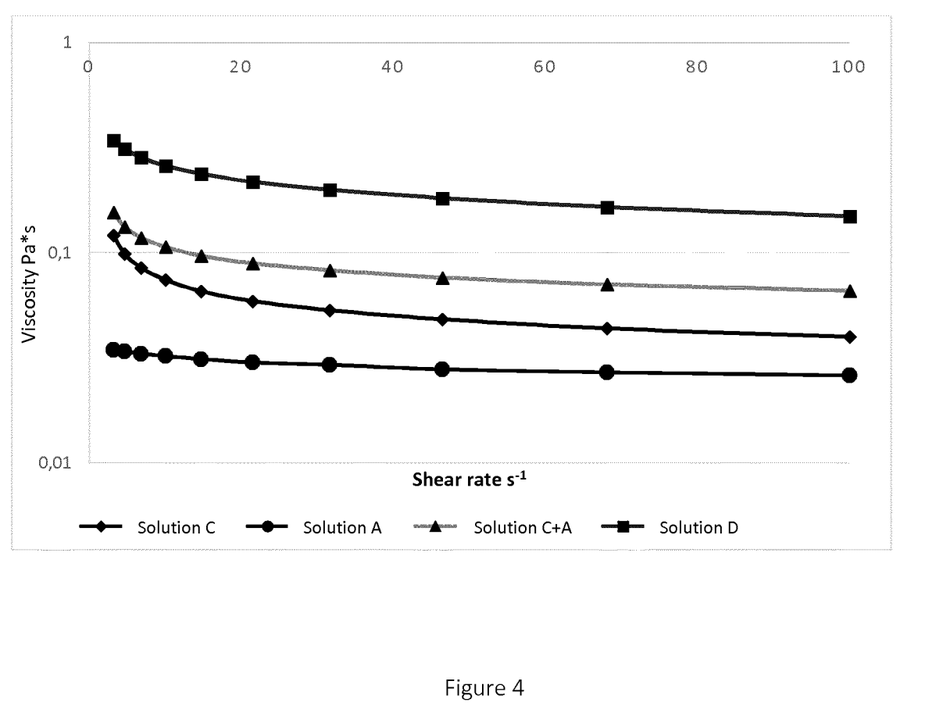
FIGS. 4 and 5 show the viscosity values for composition 1 (invention) and composition 2 (comparative) as a function of the applied shear rate as determined by the measurement of interaction with mucin.
Figure 5:
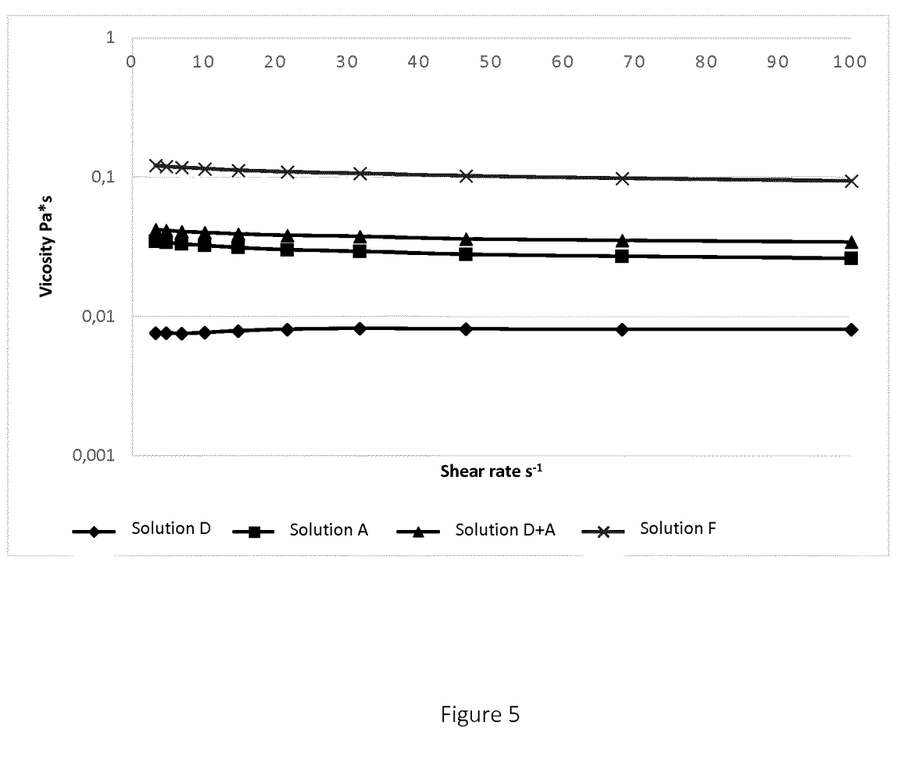

FIGS. 4 and 5 show the viscosity values for Compositions 1 and 2 as a function of the applied shear rate.

Example 5: Determination of Mucoadhesivity by Surface Adhesion Measurements

The aim of the following experiment is to evaluate and compare the adhesion capacity of the composition according to the invention (Composition 1) to the mucosa and resist to leaching with respect to the gastroprotective composition having the formulation as in Example 2 (Composition 2).

The in vivo situation was reproduced by adhering the formulations to a mucin-coated plastic surface mimicking the surface of the esophageal mucosa and measuring the amount of composition remaining adherent per surface unit.

The percentage of composition adhered to the surface is a direct indication of the feature of the composition to adhere to the oesophageal mucosa and resist to the leaching saliva.

An aqueous mucin suspension at a concentration of 12% (w/w) was homogeneously deposited on two plastic surfaces, placed at 70° C. for 45 minutes and then cooled to room temperature.

Then, 2.5 ml of Compositions 1 and 2 were homogeneously deposited on one of the two plastic surfaces with adhered mucin; the surfaces were then inclined at 90° for 6 minutes, letting the excess non-adhered composition drain away from the surface.

The percentage of composition adhering to the mucin film onto the plastic surface was calculated by the following formula:

$$\% \text{ of adherent composition} = \frac{\text{mg of remaining composition}}{\text{mg of initial composition}} \times 100$$

The adhesion values of the Composition 1 and Composition 2 were determined by the amount of each the composition adhered to the mucin film, per unit of surface.

To reproduce the effect of saliva on the swallowed composition to the esophogous, the two mucin-coated plastic surfaces, with adhered composition, were then soaked for 30 seconds in two separate beakers containing 200 ml of water and then the surfaces were inclined at 90° for 6 minutes.

Following this washing step, the amount of adhered composition per surface unit on the mucin film coating the plastic surface was determined again.

By the ratio between the amount of adherent composition before and after the washing step the percentage of weight variation due to composition lost in the washing or water absorbance is calculated.

$$\% \text{ of composition weight variation} = \frac{\text{mg composition before washing} - \text{mg composition after washing}}{\text{mg of composition before washing}} \times 100$$

TABLE 7

| Sample | Percentage of composition adhered to the mucin film % (w/w) | Amount of composition adhered for unit of surface (mg/cm²) | Amount of composition adhered for unit of surface after washing (mg/cm²) |
|---|---|---|---|
| Composition 1 | 32.0 ± 5.2 | 70.8 ± 1.0 | 72.9 ± 4.2 |
| Composition 2 | 46.0 ± 2.3 | 56.6 ± 9.1 | 56.8 ± 6.6 |

The results demonstrated that Composition 1 remains more adhered to the mucin film and resists to the drainage away than Composition 2.

Example 6: Determination of Mucoadhesivity in Ex-Vivo Models

Mucoadhesivity of Composition 1 was confirmed in an ex-vivo experimental model using swine central oesophagus tracts and compared with Composition 2 and with the commercial Gaviscon® sachet product.

The entire oesophagus in its cylindrical structure deprived of its muscular tissue was treated with swine pepsin (2000 U/ml) in a saline solution at pH 2.0. The mucosa was then washed with a saline solution. The entire cylindrical oesophagus was opened to expose the internal mucosa and divided into pieces for successive analysis.

The oesophageal mucosa fragments were divided in two groups, samples A and samples B, and were treated as reported here below.

Samples A were treated with one of the compositions to be tested (Composition 1, Composition 2, or Gaviscon®) and then coloured with Evans Blue (EB) dye, obtaining samples A1, A2 and A3, respectively.

Samples B were treated with one of the compositions to be tested (Composition 1, Composition 2, or Gaviscon®), then washed with saline solution and subsequently coloured with EB, obtaining samples B1, B2 and B3, respectively.

A reference sample was instead treated with EB only.

Two different analytical methods were performed to determine the amount of dye attached to the mucosa, i.e. a spectrophotometric analysis and an epifluorescence microscopy analysis.

A. Spectrophotometric Determination

A set of samples A and B and the reference sample, after being washed to remove the excess of dye, were dried at 37° C. for 30 minutes, weighed and then soaked in 3 ml formamide at 50° C. for 48 hours. The amount of dye extracted in the formamide solution was determined by spectrophotometric measurement, by the absorbance at 620 nm, compared to a standard curve.

Table 8 shows normalized absorbance, expressed as a difference (Δ) compared to the reference sample absorbance value, and normalized to the weight of tissue samples (expressed in mg) according to the formula:

Normalized absorbance=absorbance (Δ) (nm)/weight (mg)*1000

Higher values correspond to higher protective effect.

TABLE 8

| Sample | Normalized Abs. | Normalized Abs. after waghing |
|---|---|---|
| Composition 1 | 16.6 | 14.6 |
| Composition 2 | 19.4 | 7.9 |
| Gaviscon ® | 19.6 | 17.9 |

By Table 8 results that Composition 1 provides high protective effect.

B. Determination in Epifluorescence Microscopy Analysis

Following treatment with Composition 1, Composition 2, or Gaviscon® as above described, a set of oesophageal mucosa samples were treated with 4% (v/v) formaldehyde at pH 7.4 overnight at 4° C., then washed with phosphate buffer and finally transferred to a saccharose 25% by weight phosphate buffered solution at 4° C. The histological samples were then stored at −80° C. and then cut into serial 10 μm thick sections and placed on specimen slides. The samples were analysed by epifluorescence microscope.

The microscopic analysis of the sections revealed:
in the oesophageal mucosa, injured with swine pepsin and treated with EB only (reference sample), the dye entered the layers of the stratified squamous epithelium, affected the entire lamina, passed the muscularis mucosae layer until the submucosa;

samples treated with Composition 1 showed a very intense background colouring and the dye signal only in some layers of the stratified epithelium;

samples treated with Composition 2 showed that EB colouring was present at some epithelium layers and not in the submucosa, being intensely fluorescent in the epithelium areas with keratin;

samples treated with Gaviscon® showed EB colouring only in some epithelium layers.

Example 7: In Vitro Determination of the Protective Effect of Composition 1 and Composition 2, by Permeability Measures Caffeine is recommended as reference compound at low lipophilicity for studies of percutaneous absorption according to the Guideline for the Testing of Chemicals (OECD No. 428, Apr. 13, 2004, skin absorption, in vitro method) to evaluate the permeability. For the ability to overcome the epithelial barrier even in the absence of damage caffeine was used as a probe to assess the propensity of a given composition to form a protecting film: the reduction of the passage of caffeine through the biological tissue model is an index of film forming property.

As model of 3D epithelial tissue Reconstructed Human Esophageal Epithelium, manufactured by Episkin, France (0.5 cm$^2$ sized and 100 µm thick) was used Reconstructed Human Esophageal Epithelium samples were treated for 3 hours with test compositions: Composition 1, Composition 2, saline solution (negative control) or vaseline (positive control); 100 µL of 0.5% (w/v) caffeine solution were then applied in the apical (donor) compartment for 3 more hours. One, two and three hours after caffeine solution application the system was washed with 1 ml of saline solution and the fluid collected for further analysis.

The amount of permeated caffeine was determined by HPLC chromatographic analysis with UV-DAD detector at 275 nm, using a reverse phase column (ZORBAX Eclipse XDB-C18) with 5 µm diameter particles and 150×4.6 mm size.

Caffeine was eluted with: phase A, ammonium acetate 10 mM; phase B, acetonitrile/methanol 1:1, with linear gradient, from 20% to 80% phase B in 10 minutes. The determination of caffeine was performed with a calibration curve.

Table 9 reports the percentage of caffeine penetrated through the membrane.

TABLE 9

| | Caffeine penetrated in Oesophageal Epithelium model % (w/w) | | | |
|---|---|---|---|---|
| Time | Saline solution | Vaseline | Composition 1 | Composition 2 |
| T = 1 h | 31.68 ± 2.62 | 9.38 ± 0.03 | 12.42 ± 0.01 | 14.90 ± 0.03 |
| T = 2 h | 20.12 ± 0.04 | 0.00 ± 0.00 | 13.33 ± 0.05 | 15.99 ± 0.05 |
| T = 3 h | 12.43 ± 0.01 | 0.00 ± 0.00 | 13.16 ± 0.04 | 15.29 ± 0.04 |

Results confirmed the filming efficacy of Composition 1, which enables a reduction in caffeine permeation through the 3D epithelium model greater than Composition 2.

Example 8: Determination of Barrier Function by Trans-Epithelial Electrical Resistance (TEER) Measurement of Composition 1 and Composition 2

Trans-Epithelial Electrical Resistance (TEER) is the measure of the movement of ions across the paracellular pathway regulated by polarized plasma membrane surfaces and cell-to-cell tight junctions that together prevent movement of solutes and ions across the epithelia. Thus, TEER provides an indirect assessment of tight junction stability and direct measure of the functionality of the barrier-function in epithelial tissue, providing information on the overall resistance of the epithelium layer.

The assessment of the barrier function of the testing composition was performed by measuring the trans-epithelial electrical resistance of the same 3D epithelium samples, prepared and used as described in Example 7, when applying an alternating current at 12.5 HZ frequency, then a washing was performed to remove the compositions under examination and caffeine after the 6 hours treatment.

Table 10 reports the TEER values of the samples treated with Compositions 1 and 2 compared to those treated with saline solution and Vaseline, at time zero ($T_0$) and at the end of treatment (T=6 h).

TABLE 10

| Resistance per unit surface (ohm * cm$^2$) | Saline solution | Vaseline | Composition 1 | Composition 2 |
|---|---|---|---|---|
| T = 0 | 56.72 | 57.61 | 62.00 | 60.72 |
| T = 6 h | 60.89 | 61.33 | 57.17 | 53.06 |

Trans-epithelial electrical resistance (TEER) data confirm that the composition of the invention (Composition 1) does not influence paracellular flow through the epithelial mucosa and maintains functional integrity even after treatment.

Example 9: Determination of Membrane Integrity Through Fluorescence Measure of Composition 1 and Composition 2

Lucifer Yellow is a fluorescent dye which the cell membrane is impermeable to: it is used to study the paracellular permeability of a substance: When the junctions are intact Lucifer Yellow has a very low permeability, if the junctions are damaged Lucifer Yellow flow increases. Therefore, Lucifer Yellow assay is used to verify the integrity of cell junctions in the presence of compositions to be evaluated, in this case after treatment with Compositions 1 and 2 and the controls. The experiment was performed on Reconstructed Human Oesophageal Epithelium samples prepared as described in Example 8.

A volume of 0.5 ml of Lucifer Yellow (500 µM in saline solution) was applied to the apical compartment of membrane samples (treated with Composition 1, Composition 2, saline solution or vaseline), and 1 ml of saline solution was added to the basolateral compartment. After one hour of incubation at 37° C. the transport of dye from the apical to the basolateral compartment was assessed by the measurement of the fluorescence of apical compartment at time zero (t=0). At the end of the 1 hour incubation, the fluorescence of the basolateral compartment was measured. The measures were obtained by spectrofluorimeter (TECAN INFINITE M200) with 428 nm excitation and 535 nm emission.

Table 11 reports the percent flow of Lucifer Yellow from the apical compartment to the basolateral compartment calculated by applying the following formula:

$$\frac{\text{Basolateral fluorescence}}{\text{Apical fluorescence } (t=0)} * 100 = \text{Lucifer Yellow Flow (\%)}$$

TABLE 11

| | Lucifer Yellow Flow (%) |
|---|---|
| Saline solution | 8.38 |
| Vaseline | 8.57 |
| Composition 1 | 8.10 |
| Composition 2 | 9.19 |

The results showed that there is no significant difference between samples treated with Compositions 1, 2, negative or positive control, confirming that both compositions maintain the barrier integrity and the functionality of cell junctions.

Example 10: Determination of Stability of Composition 1

Composition 1, divided in sachets, was analysed for stability at 25° C. and 40° C. at 1 (T1) and 3 (T3) months and compared with the composition at time zero ($T_0$).

The stability was determined through pH and density measurements, and the assessment of the composition appearance, according to Table 12.

TABLE 12

| | $T_0$ | T1 (25° C.) | T1 (40° C.) | T3 (25° C.) | T3 (40° C.) |
|---|---|---|---|---|---|
| Appearance | transparent | transparent | transparent | transparent | transparent |
| pH | 5.4 | 5.5 | 5.4 | 5.5 | 5.4 |
| Density (g/ml) | 1.07 | 1.07 | 1.07 | 1.07 | 1.07 |

Example 11: Clinical Study

A preliminary, randomized, two parallel groups, clinical study was performed to evaluate the effect of the administration of Composition 1 prepared according to Example 1, on the typical symptoms referred by non-erosive gastro-oesophageal reflux disease (NERD) patients.

For the study non-erosive gastro-oesophageal reflux disease (NERD), adult (aged >18 years), both male and female, patients with typical reflux symptoms, i.e. heartburn, acid regurgitation, retrosternal pain and acid taste in the mouth were enrolled. At least two of the above symptoms should have been present in the last three months and at least three times a week in the month preceding the study screening visit. The diagnosis of NERD was based on the absence of macroscopic lesions of oesophageal mucosa at endoscopy, and by the positivity of a questionnaire to evaluate the symptoms severity.

Two patients received Composition 1, in stick pack 10 ml BID and two patients received Composition 1 in stick pack 10 ml TID.

Primary end point of the study was the reduction of the typical reflux symptoms at the end of the treatment period (14 days) with respect to the baseline determined at T0, assessed using Reflux Disease Questionnaire—RDQ score.

All the patients who received Composition 1 BID or TID had a beneficial effect on the reduction of the atypical symptoms associated to NERD, such as, hoarseness and irritating cough with an increased QOL at demonstration that the efficacy of this composition is provided also a low daily administrations.

The invention claimed is:

1. Method of mitigating gastroesophageal reflux in subjects in need thereof, said method comprising:
administering to said subjects a mucoadhesive composition comprising chondroitin sulphate at a concentration from 0.5 to 5% (w/v), xyloglucan at a concentration from 0.05 to 5% (w/v), glycerol at a concentration from 10 to 70% (w/v), wherein the v refers to the volume of the final composition, and optionally pharmaceutically acceptable excipients, wherein a viscosity of equal to or higher than 0.15 Pa·s at shear rate of 100 $s^{-1}$ or less is detected in the presence of mucin.

2. The method according to claim 1, wherein said composition comprises chondroitin sulphate at a concentration from 1 to 5% (w/v), xyloglucan at a concentration from 0.1 to 1% (w/v), glycerol at a concentration from 10 to 50% (w/v), wherein the v refers to the volume of the final composition and optionally pharmaceutically acceptable excipients.

3. The method according to claim 2, wherein said composition comprises sodium chondroitin sulphate from 0.1 to 0.5 g, xyloglucan from 0.01 to 0.1 g, glycerol from 1 to 5 g, and pharmaceutically acceptable excipients including water up to a volume of 10 ml.

4. The method according to claim 3, wherein said composition comprises sodium chondroitin sulphate 0.3 g, xyloglucan 0.04 g, glycerol 2 g, and said excipients comprising sodium bicarbonate 0.01 g, xanthan gum 0.0083 g, xylitol 0.2 g, sodium benzoate 0.02 g, orange flavor 0.015 g, citric acid 0.01 g, potassium sorbate 0.02 g, hydroxypropyl methylcellulose 0.086 g and water up to a volume of 10 ml.

5. The method according to claim 1, wherein said composition is in unit dosage form or in syrup for oral administration.

6. The method according to claim 1, wherein said composition has viscosity values from 1 to 15 pa·s when subjected to shear rates from 0 to 1.5 $s^{-1}$, and viscosities lower than 1.5 pa·s when subjected to shear rates higher than 1.5 $s^{-1}$ in the absence of mucin.

7. The method according to claim 1, wherein said composition has pH values from 4.5 to 6.5.

8. The method according to claim 1, wherein the xyloglucan is a purified xyloglucan.

9. The method according to claim 1, wherein said composition is for the preparation of pharmaceutical products or medical devices for oral administration.

10. The method according to claim 1, wherein the gastroesophageal reflux is of erosive or non-erosive type, and causes pathologies selected from the group consisting of oesophagitis, damages to duodenal endothelium, erosions, ulcers and gastritis.

11. The method according to claim 4, wherein said composition is administered twice daily.

12. The method according to claim 4, wherein said composition is administered three times daily.

13. The method according to claim 4, wherein the gastroesophageal reflux is non-erosive gastro-esophageal reflux disease.

* * * * *